US010769966B2

(12) United States Patent
Sebro

(10) Patent No.: US 10,769,966 B2
(45) Date of Patent: Sep. 8, 2020

(54) APPARATUS AND METHOD OF SIMULATING CARDIAC PHENOMENA

(71) Applicant: Nadew Sebro, Chicago, IL (US)

(72) Inventor: Nadew Sebro, Chicago, IL (US)

(*) Notice: Subject to any disclaimer, the term of this patent is extended or adjusted under 35 U.S.C. 154(b) by 424 days.

(21) Appl. No.: 15/947,817

(22) Filed: Apr. 8, 2018

(65) Prior Publication Data

US 2019/0311653 A1    Oct. 10, 2019

(51) Int. Cl.
*G09B 23/30* (2006.01)
*G16H 50/50* (2018.01)
*G06F 30/20* (2020.01)

(52) U.S. Cl.
CPC .......... *G09B 23/30* (2013.01); *G16H 50/50* (2018.01); *G06F 30/20* (2020.01)

(58) Field of Classification Search
CPC .... G09B 23/28; G09B 23/281; G09B 23/283; G09B 23/286; G09B 23/288; G09B 23/30; G09B 23/3288; G06F 30/20
See application file for complete search history.

(56) References Cited

U.S. PATENT DOCUMENTS

| | | | | |
|---|---|---|---|---|
| 5,041,973 A | * | 8/1991 | Lebron | A61B 5/04021 703/11 |
| 5,482,472 A | * | 1/1996 | Garoni | G09B 23/30 345/83 |
| 7,220,127 B2 | * | 5/2007 | Ellingson | G09B 23/30 434/272 |
| 8,727,786 B2 | * | 5/2014 | Hill | G09B 23/30 434/267 |

* cited by examiner

*Primary Examiner* — Timothy A Musselman
(74) *Attorney, Agent, or Firm* — AU LLC; Adam E. Urbanczyk

(57) ABSTRACT

The present invention relates to an apparatus for simulating electrocardial phenomena and related pathologies. A physical replica of a heart is provided with series of light emitters representing actual and conceptual electrocardial pathways, and controls therefor and output thereof, allowing the demonstration and graphical representation of electrocardial phenomena.

17 Claims, 5 Drawing Sheets

APPARATUS AND METHOD OF SIMULATING CARDIAC PHENOMENA

FIELD OF THE INVENTION

The present disclosure is generally related to simulation of cardiac activities, and more particularly related to simulation of cardiac activities in a three-dimensional (3D) replica heart.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Electrocardiogram (ECG or EKG) is extensively used for determining the condition of a patient's heart. Among many heart conditions, the most lethal and treatable form of myocardial infarctions (i.e. heart attacks), ST-elevation MI, is diagnosed only through accurate analysis of the EKG. Reading the EKG involves two discrete functions: description and interpretation. Description implies identifying individual geometric patterns and defining a suitable terminology. Interpretation involves associating descriptions with anatomical structures in the patient's heart along with physiological and pathophysiological activities, and determining a heart condition responsible for such findings.

Interpreting an exact heart condition of a patient by accurate analysis of the EKG requires years of rigorous training. According to the American College of Cardiology, it requires a minimum of 36 months of training with a suggested 3,500 supervised EKG reads to become an expert in interpreting from the EKGs. The 12-lead EKG detects and records electrical activity of a heart using 12 leads, or sensors. The number of sensors and inherent complexity of concurrent cellular, tissue, and organ-level cardiac electrophysiologic phenomena make describing and interpreting a 12 lead-generated EKG a complex task.

Conventionally-available training to understand the 12-lead EKG suffers from many limitations. These limitations primarily stem from existing methods defying Classic Learning Theory by not overlapping new information with existing knowledge, whereby either learners do not have an opportunity to first identify what they know or are not provided with adequate opportunity to overlap new information with existing information or are not empowered to control the overlap process (sequence, tempo, emphasis and frequency). For example, most commercially available EKG simulators include components only for a menu of electrophysiological rhythm names and a display screen for EKG rhythms, without inclusion of physical replica of the human heart to reflect the corresponding source anatomy and a visual representation of physiologic processes reflecting underlying events. This deficiency takes away a vital opportunity from learners to overlap the new information (e.g., EKG Rhythm) with existing knowledge (e.g., anatomy and physiology), which medical students may spend an entire year learning. Another example of limitations with existing educational models, even those encompassing replica of the heart, is not having a pace control button to control the tempo of the visual input since a heart on average beats at a rate of 80 beats per min and identifying individual waves of a cardiac cycle in tachyarrhythmia becomes difficult due to overlap of waves from overcrowding at higher heart rates.

Thus, in consideration of the above limitations, there remains a need of an interactive learner-controlled technique for improved understanding of the EKG and cardiac activities associated with interpretations made from the EKG.

SUMMARY OF THE INVENTION

It will be understood that this disclosure is not limited to the particular systems, apparatus, and methodologies described, as there can be multiple possible embodiments of the present disclosure which are not expressly illustrated in the present disclosure. It is also to be understood that the terminology used in the description is for the purpose of describing the particular versions or embodiments only and is not intended to limit the scope of the present disclosure.

In an example embodiment, an apparatus for simulating different electrical, other physiologic, and pathophysiologic phenomena is described. The apparatus comprises a microcontroller. The microcontroller comprises one or more CPUs (processor cores) along with memory and programmable input/output peripherals to simulate electrical, other physiologic, and pathophysiologic patterns for the different conditions of the heart. The apparatus further comprises a plurality of nodes connected along an electrical pathway corresponding to an actual or conceptual electrical signal pathway of a living heart. The apparatus further comprises a plurality of light emitters demonstrating at least one cardiac electrophysiologic pattern of stored cardiac electrophysiologic patterns, based on a user input.

In another example embodiment, a method of simulating different cardiac electrophysiologic phenomena is described. The method comprises storing, in a memory of a microcontroller, electrical, other physiologic and pathophysiologic patterns for the different conditions of the heart. The method further comprises providing a plurality of nodes connected along an electrical pathway corresponding to an actual or conceptual electrical pathway of a living heart. The method further comprises demonstrating, using a plurality of light emitters, at least one cardiac electrophysiologic pattern of stored cardiac electrophysiologic patterns, based on a user input.

BRIEF DESCRIPTION OF THE DRAWINGS

The accompanying figures and drawings, incorporated into and forming part of the specification, service to further illustrate the present invention, its various principles and advantages, and varying embodiments. It is to be noted, however, that the accompanying figures illustrate only typical embodiments of the present invention and are not to be considered limiting of its scope as the present invention may admit other equally effective embodiments.

DETAILED DESCRIPTION OF THE INVENTION

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Figure 1:
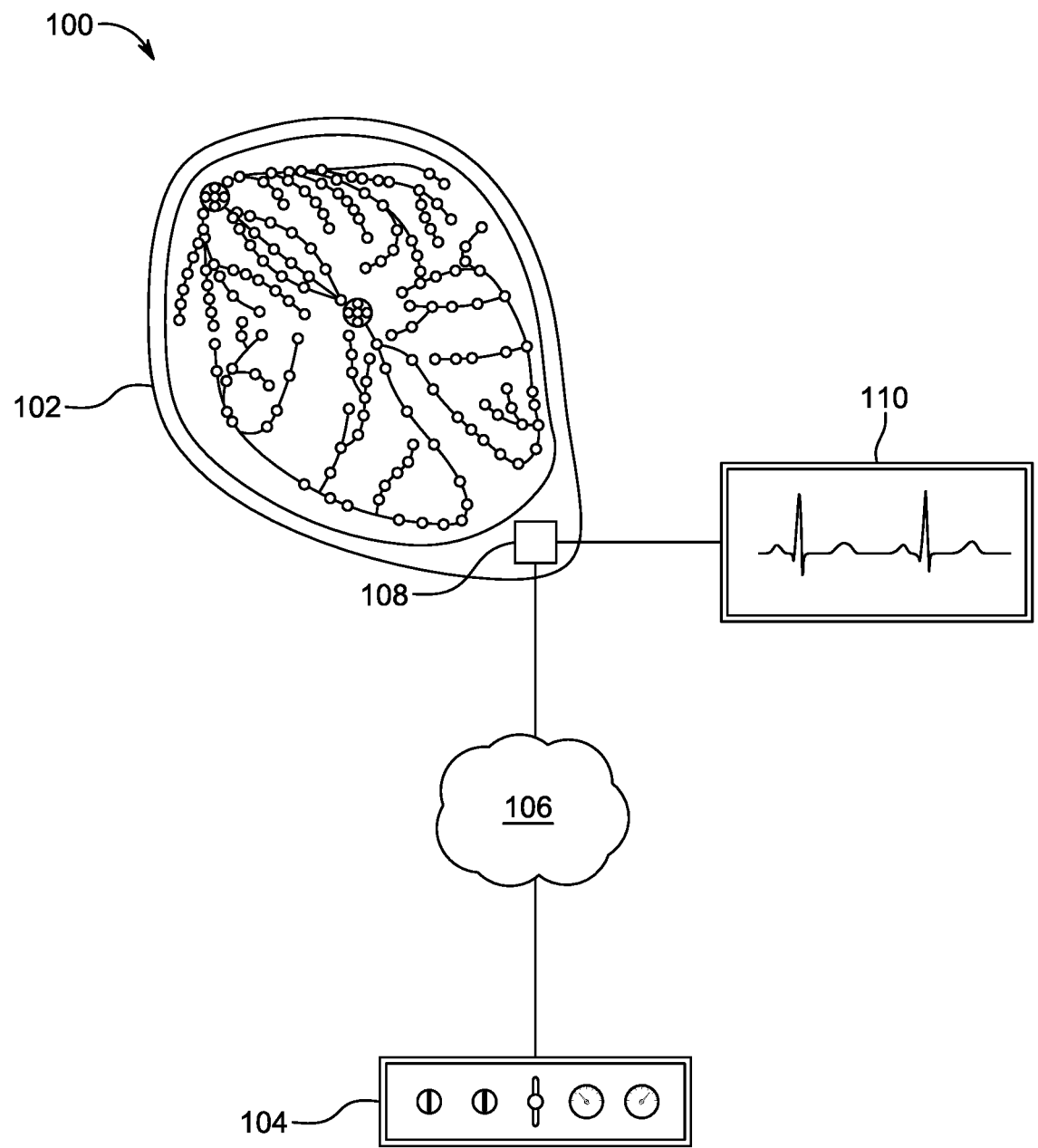
FIG. 1 illustrates a connection diagram 100 of an apparatus 102 for simulating different electrical, other physiologic and pathophysiologic patterns for different conditions of a human heart.

FIG. 1 illustrates a connection diagram 100 of an apparatus 102 for simulating different activities of a heart, according to an embodiment. FIG. 1 illustrates the apparatus 102 connected to a control panel 104 through a communication network 106. The control panel 104 comprises several control knobs for providing different user inputs to the apparatus 102. All devices or modules communicating with the apparatus 102 indicate communicating with a microcontroller 108 present in and/or controlling the apparatus 102.

The communication network 106 is implemented using either of a wired or wireless communication technique. The wireless communication technique can be selected from visible light communication (VLC), worldwide interoperability for microwave access (WiMAX), long term evolution (LTE), wireless local area network (WLAN), infrared (IR) communication, public switched telephone network (PSTN), integrated services digital network (ISDN), broadband, cellular, optical fiber network, and radio waves.

The microcontroller 108 executes an algorithm, stored in a memory of the microcontroller 108, for simulating different conditions of a heart. The microcontroller 108 is also configured to decode and execute any instructions received from the controller 104 or one or more input peripherals. The microcontroller 108 can be a general-purpose processor (e.g., Intel microprocessor) and/or one or more special purpose processors (e.g., digital signal processors or Xilinx System On Chip (SOC) field programmable gate array (FPGA) processor). The microcontroller 108 is configured to execute one or more algorithms to carry out any of the functions described in this description.

In one embodiment, the apparatus 102 is used for simulating different physiological cardiac events, cardiac pathologies, and cardiac electrophysiologic phenomena of a human heart, heart of an animal, bird, amphibian, or other organisms comprising a chambered heart. Further, the instructions stored and processed by the microcontroller 108 of the apparatus 102 refer to the different physiological cardiac events, cardiac pathologies, and cardiac electrophysiologic patterns corresponding to different cardiac activities. The different physiological cardiac events, cardiac pathologies, and cardiac electro physiologic mechanisms including but not limited to stopping, slowing down, speeding up electrical signal conductions, creating a bypass, creating electrical signal reentry and initiating normal and altered ectopic event.

In one embodiment, the apparatus 102 comprises a transparent shell having a shape replicating a human heart. The transparent shell is used to provide better visualization of the physiological cardiac events, the cardiac pathologies, and cardiac electrophysiologic phenomena, e.g., progress of cardiac electrophysiologic patterns across different sections of the human heart. Further, the transparent shell is made up of glass, plastic, or transparent composite which allow the user sufficient visual access to the interior electrical pathways.

Figure 2:
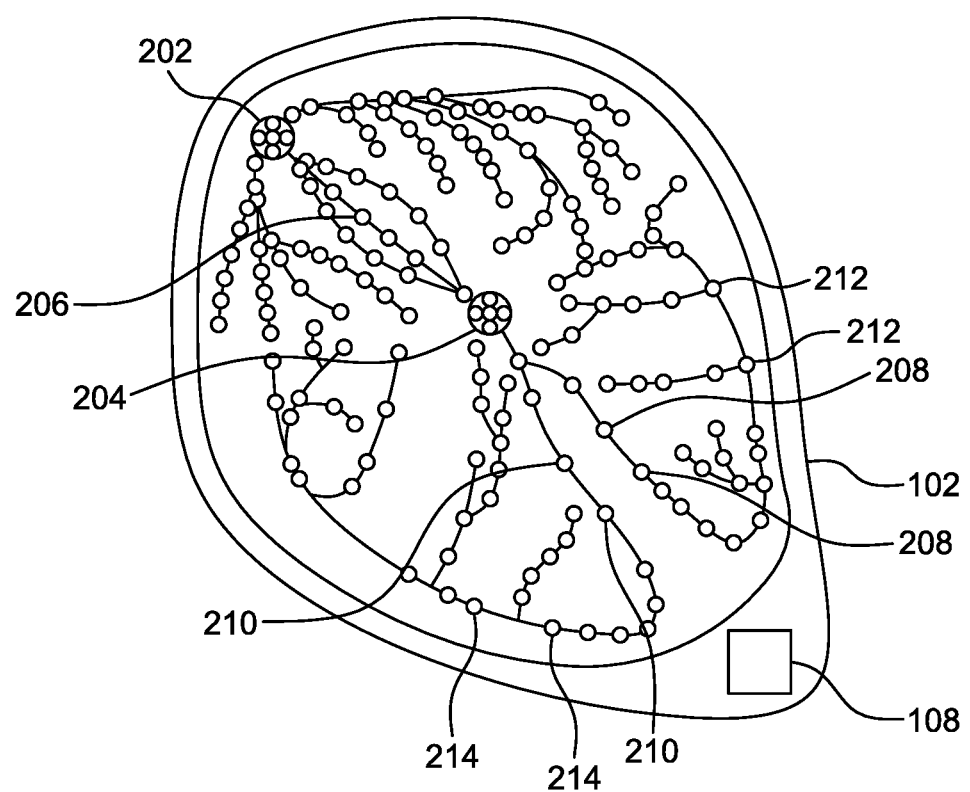
FIG. 2 illustrates electrical impulse transfer in the apparatus 102 for simulating different activities of a human heart, according to an embodiment.

FIG. 2 illustrates electrical impulse transfer in the apparatus 102 for simulating different activities of the human heart, according to an embodiment. The electrical impulse transfer takes place along nodes 202-214 connected along an electrical pathway corresponding to an actual electrical pathway of a living heart. The node 202 represents Sinoatrial (SA) node of the human heart, node 204 represents Atrioventricular (AV) node of the human heart, and node 206 represents an intermediary node present between the SA node and the AV node. Nodes 208 are present along locations of Right Bundle of His and nodes 210 are present along positions of Left Bundle of His. Nodes 212 and 214 are present along positions of Right Purkinje fibers and Left Purkinje fibers respectively. A few nodes are illustrated in the FIG. 2 for ease of representation; however, numerous nodes could be present in the apparatus 102.

In one embodiment, light emitters are placed along each of the nodes 202-212. The light emitters are used to demonstrate the different physiological cardiac events, cardiac pathologies, and cardiac electrophysiologic patterns. In one example, the light emitters are light emitting diodes (LEDs). The color of each LED can be selected for better visualization of the different physiological cardiac events, cardiac pathologies, and cardiac electrophysiologic patterns.

In one embodiment, a cardiac electrophysiologic pattern is demonstrated based on a user input. The user input, in one case, is provided through the controller 104. The user input comprises an action corresponding to the different activities of the human heart. The action can comprise stopping, slowing down, speeding up, creating a bypass, and initiating an ectopic event. In another case, the user input is provided through a user device connected to the apparatus 102. The user device provides a user interface, using which the user input may be provided. The user device may be connected via a wired or wireless connection. Further, the user device is one of a smart phone, laptop, desktop, tablet, phablet, or any other user operable electronic device.

In one embodiment, the user input may correspond to demonstration of the electrical impulse transfer in a healthy human heart. In a healthy human heart, the electrical impulse originates at the SA node, travels to the AV node, passes through the Right and Left bundle of His, reaches the Right and Left Purkinje fibers, and propagates through the Left and Right bundles and their respective fascicles. Such movement of the electrical impulse is shown by glowing the LEDs present around the nodes present at respective locations. Thus, by successive glowing of the LEDs, the electrical impulse is shown to be initiating at the node 202, reaching the node 204 by passing through the node 206, simultaneously reaching the nodes 208 and 210, and finally reaching the nodes 212 and 214.

In one embodiment, based on the different cardiac electrophysiologic patterns followed during the electrical impulse transfer, different anomalies related to functioning of the human heart are demonstrated. As previously mentioned, the different cardiac electrophysiologic patterns are demonstrated based on the user input provided through the control panel 104. The different disorders related to functioning of the heart include, without limitation Premature Atrial Contraction (PAC), Supraventricular Tachycardia (SVT), sick sinus syndrome, Wolff-Parkinson-White (WPW) syndrome, atrial fibrillation, atrial flutter, ventricular fibrillation, ventricular tachycardia and other brady- and tachyarrhythmias. Similarly, the cardiac electrophysiologic patterns followed during other heart disorders can also be demonstrated using the apparatus 102.

In one embodiment, interconnection of the nodes 202-214 by an operator may refer to the user input, used to demonstrate a cardiac electrophysiologic pattern. In one case, the nodes are push buttons, operated by the operator for completing the electrical pathways. Each complete electrical pathway corresponds to a regular or irregular functioning of the human heart.

In another case, the operator connects the nodes 202 and 206 using an interconnection means. During such case, the electrical impulse appears to originate from the node 206. This can refer to improper functioning of the SA node, which can lead to sinus bradycardia, sinus arrest, sinoatrial blockage, and tachycardia-bradycardia syndrome. Such improper functioning of the SA node is thus demonstrated by interconnecting the nodes 202 and 206. Similarly, the operator can interconnect other nodes to demonstrate other cardiac electrophysiologic patterns or anomalies related to the human heart.

In yet another case, the operator connects the nodes 212 and 204 to demonstrate reentry in the human heart. Reentry refers to a process of improper conduction of the electrical impulse in the human heart. During reentry, the electrical impulse recirculates in the human heart and causes repetitive excitation of heart muscles. Reentry can lead to abnormal heartbeat conditions, identified as arrhythmias or dysrhythmias. Thus, connection of the nodes 212 and 204 results in recirculation of the electrical impulse and demonstrates global reentry by the apparatus 102. Similarly, other anomalies related to the human heart, such as automaticity and triggered activity, can also be demonstrated through the apparatus 102.

The apparatus 102 is further connected with a display device 110, as shown in the FIG. 1. The display device 110 can be any of a smart phone, laptop, desktop, tablet, and display screen. The display screen 110 is used for illustrating an EKG wave corresponding to each cardiac electrophysiologic pattern demonstrated using the apparatus 102. In one case, an electrocardiograph is used in place of the display device 110.

Figure 3:
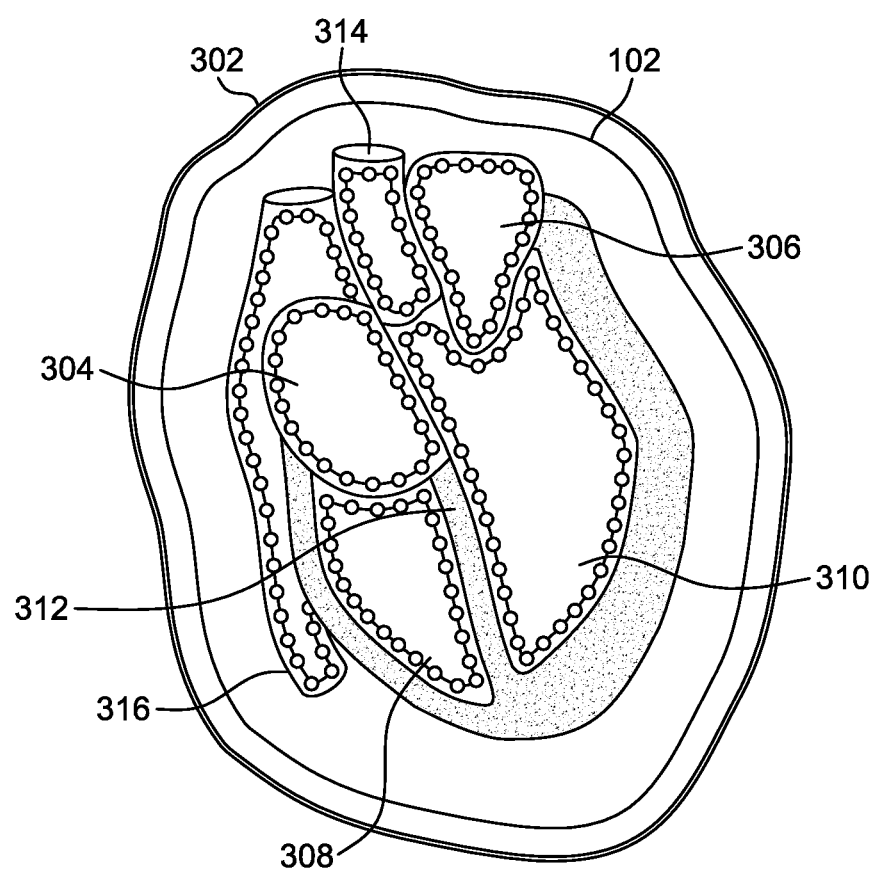
FIG. 3 illustrates a transparent shell enclosing the apparatus 102 to represent different areas related to a human heart.

In one embodiment, the transparent shell 302 enclosing the apparatus 102 illustrates different areas related to the human heart, as shown in FIG. 3. The transparent shell 302 represents multiple areas 304-310, corresponding to at least one of cardiac anatomical references and cardiac disease patterns. The multiple areas 304-310 comprise groups of light emitters for demonstrating different cardiac pathologies, as shown in FIG. 3. In this embodiment, area 304 represents a right atrium, area 306 represents a left atrium, area 308 represents a right ventricle, and area 310 represents a left ventricle, of the human heart.

In one case, light emitters of the area 304 glowing at first and successive glowing of light emitters of the area 308 for a sufficient amount of time (e.g. 1 second) indicate blood flow from the right atrium to the right ventricle. Such operation indicates proper functioning of the human heart. In another case, light emitters of the area 304 glowing for a shorter time interval and successive glowing of light emitters of the area 308 indicates abnormal heart valve present between the right auricle and the right ventricle. Similarly, light emitters are also present in other regions representing different blood vessels, such as 312, 314, and 316, as shown in FIG. 3. In one case, light emitters of the area 312 glowing for a longer time interval could indicate atherosclerosis or atherosclerosis in the blood vessel "Left Anterior Descending Artery." In a similar manner, the groups of light emitters could be implemented in other areas and blood vessels of the human heart for demonstrating other cardiac pathologies.

In this fashion, an interactive technique and an apparatus 102 are provided for improved understanding of the EKG and cardiac activities associated with interpretations made from the EKG.

Figure 4:
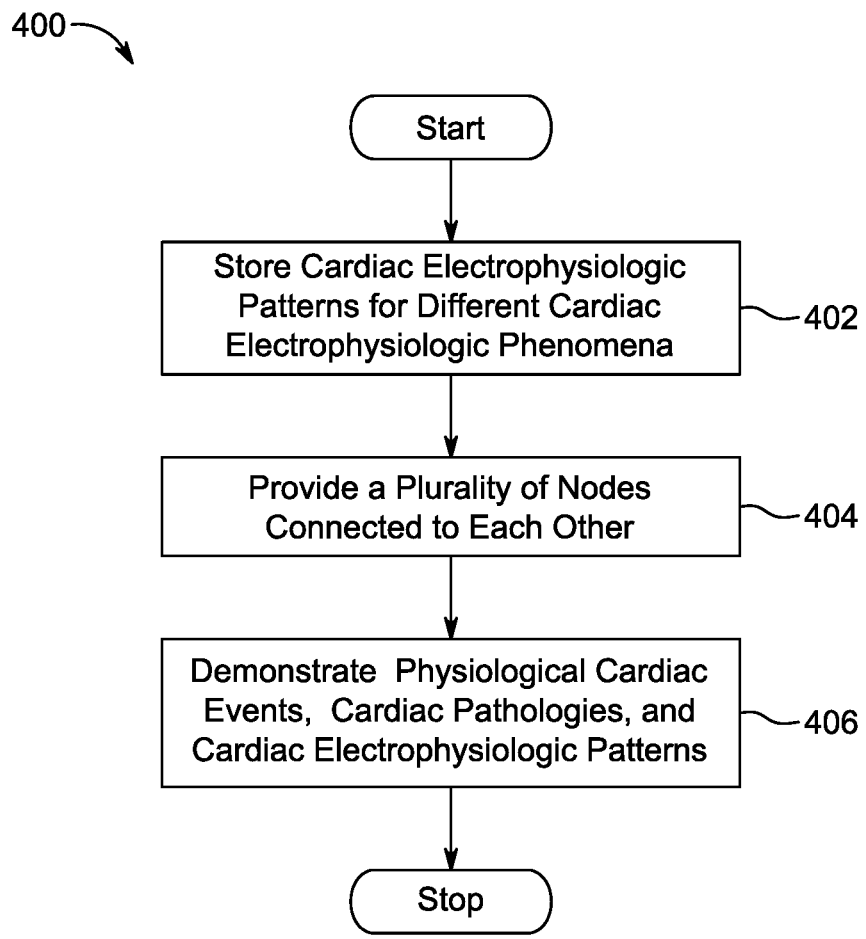
FIG. 4 illustrates a flowchart 400 of a method of simulating different activities of a heart, according to an embodiment.

FIG. 4 illustrates a flowchart 400 of simulating different activities of a heart, according to an embodiment. FIG. 4 comprises a flowchart 400 that is explained in conjunction with the elements disclosed in FIG. 1. The flowchart 400 of FIG. 4 shows the architecture, functionality, and operation for simulating different activities of the heart. In this regard, each block may represent a module, segment, or portion of code, which comprises one or more executable instructions for implementing the specified logical function(s). It should also be noted that in some alternative implementations, the functions noted in the blocks may occur out of the order noted in the drawings. For example, two blocks shown in succession in FIG. 4 may in fact be executed substantially concurrently or the blocks may sometimes be executed in the reverse order, depending upon the functionality involved. Any process descriptions or blocks in flowcharts should be understood as representing modules, segments, or portions of code which include one or more executable instructions for implementing specific logical functions or steps in the process, and alternate implementations are included within the scope of the example embodiments in which functions may be executed out of order from that shown or discussed, including substantially concurrently or in reverse order, depending on the functionality involved. In addition, the process descriptions or blocks in flow charts should be understood as representing decisions made by a hardware structure such as a state machine. The flowchart 400 starts at the step 402 and proceeds to step 406.

At step 402, cardiac electrophysiologic patterns for different cardiac electrophysiologic phenomena are stored. Further, physiological cardiac events and related pathologies are also stored. The physiological cardiac events, the related pathologies, and the cardiac electrophysiologic patterns are stored in a memory of a microcontroller 108, in one embodiment, At step 404, a plurality of nodes is provided. The plurality of nodes are connected along an electrical pathway corresponding to an actual electrical pathway of a living heart, in one embodiment.

At step 406, at least one of the physiological cardiac events, the cardiac pathologies, and the cardiac electrophysiologic patterns are demonstrated using light emitters. In one case, the light emitters comprise light emitting diodes (LEDs) positioned around the plurality of nodes. Further, at least one of the physiological cardiac events, the cardiac pathologies, and the cardiac electrophysiologic pattern can be demonstrated based on a user input, in one embodiment.

Figure 5:
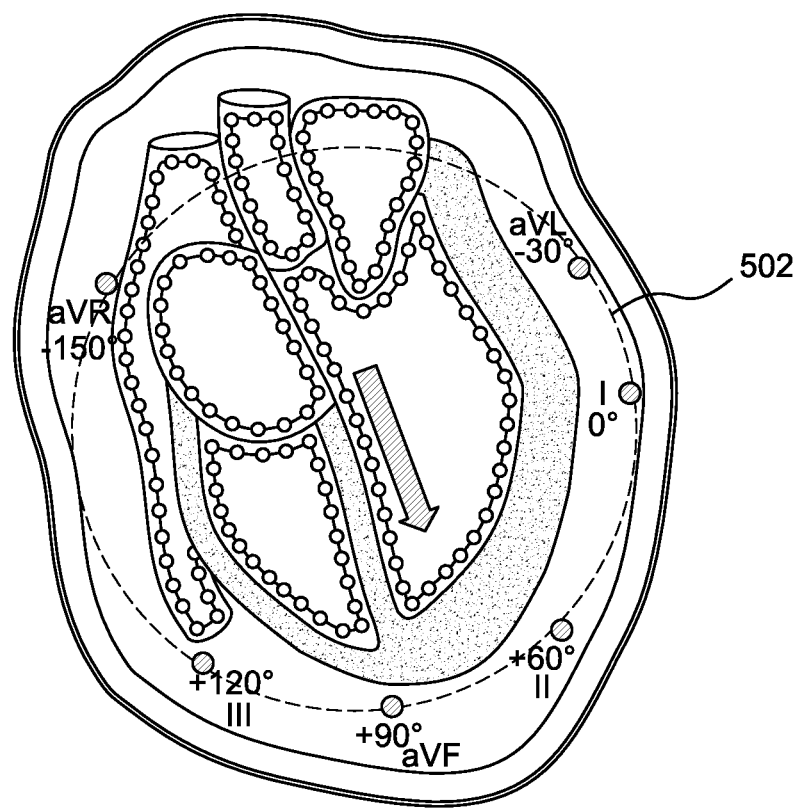
FIG. 5 illustrates a transparent shell enclosing the apparatus 102 for simulating cardiac axis phenomena.

FIG. 5 illustrates an exemplary embodiment of the apparatus 102 for simulating cardiac axis phenomenon. Referring to FIG. 5, the apparatus 102 shows a visual simulation of the cardiac axis created by the light emitters. The cardiac axis simulation within the apparatus 102 is represented using light emitters organized into two elements: a circular ring 502 with a calibration mechanism for reference on its periphery and a cardiac vector illustrated as an arrow. The cardiac vector emanates from the central area i.e. isoelectric point of the circular ring 502 and points to a specific point on the circular ring 502. The calibration mechanism on the circular ring 502 follows conventional Cabrera's Circle format, in which negative degrees values (0° to −180°) are present above a horizontal axis and positive degrees (0° to +180°) values are present below the horizontal axis. The circular ring 502 also comprises markings at a varying interval for each limb leads. The markings include aVL at −30°, I at 0°, II at +60°, aVF at +90°, III at 120°, and aVR at −150°. Although the default cardiac axis represents mean ventricular electrical axis, axis for each wave could also be demonstrated in the apparatus 102. Further, an operator could change the axis using physical knobs/buttons present on the apparatus 102 or the control knobs present on the control panel 104 to see impact of axis change on a selected rhythm on display. Similarly, the operator could change the rhythm and may observe its impact on the cardiac axis. An algorithm may be present in the microcontroller 108 for each rhythm corresponding to a matching cardiac axis. In one case, the visual simulation of the cardiac axis could be enabled or disabled using a toggle function and manipulated with help of the microcontroller 108.

Although the above detailed descriptions relate to specific preferred embodiments as the inventor presently contemplates, it will be understood that the invention in its broad aspects includes mechanical, chemical, and functional equivalents of the elements described herein. Various details of design and construction may be modified without departing from the true spirit and scope of the invention which is set forth in the following claims. Other embodiments, which will be apparent to those skilled in the art and which practice the teachings herein set forth, are intended to be within the scope and spirit of the invention.

I claim:

1. An apparatus for simulating different activities of a heart, the apparatus comprising:
    a microcontroller comprising a memory for storing data, the data comprising physiological cardiac events, cardiac axes, cardiac pathologies, cardiac electrophysiological patterns related to physiological cardiac events, and cardiac electrophysiological patterns related to cardiac pathologies;
    a first plurality of nodes connected along a first electrical pathway corresponding to an actual electrical network of a living heart;
    a second plurality of nodes connected along a second electrical pathway corresponding to a conceptual electrical phenomenon of a living heart; and
    a first plurality of light emitters disposed along the first electrical pathway, the first plurality of light emitters demonstrating at least one of the physiological cardiac events, cardiac axes, cardiac pathologies, cardiac electrophysiological patterns related to physiological cardiac events, and cardiac electrophysiological patterns related to cardiac pathologies, based on a user input.

2. The apparatus of claim 1, further comprising a transparent shell having a shape replicating a human heart.

3. The apparatus of claim 2, wherein the transparent shell is divided into multiple areas corresponding to at least two cardiac anatomical reference, wherein the multiple areas comprise a third group of light emitters, the third group of light emitters demonstrating different cardiac pathologies based on the user input.

4. The apparatus of claim 1, wherein the conceptual electrical phenomenon of a living heart is a cardiac axis.

5. The apparatus of claim 4, further comprising a second plurality of light emitters disposed along the second electrical pathway, the second plurality of light emitters demonstrating a cardiac axis vector based on user input.

6. The apparatus of claim 1, wherein the microcontroller is connected to a display device for illustrating an electrocardiogram corresponding to at least one of the physiological cardiac events, cardiac axes, cardiac pathologies, cardiac electrophysiological patterns related to physiological cardiac events, and cardiac electrophysiological patterns related to cardiac pathologies.

7. The apparatus of claim 1, wherein at least two of the first plurality of nodes are each in electrical communication with a button operable by the user for completing the first electrical pathway, and wherein the complete electrical pathway corresponds to at least one of the physiological cardiac events, cardiac axes, cardiac pathologies, cardiac electrophysiological patterns related to physiological cardiac events, and cardiac electrophysiological patterns related to cardiac pathologies.

8. The apparatus of claim 1, wherein the first plurality of light emitters are light emitting diodes.

9. The apparatus of claim 1, wherein the user input is provided using a control panel connected to the microcontroller.

10. A method of simulating different activities of a heart, the method comprising:
    storing, in a memory of a microcontroller, data comprising physiological cardiac events, cardiac axes, cardiac pathologies, cardiac electrophysiological patterns related to physiological cardiac events, and cardiac electrophysiological patterns related to cardiac pathologies;
    providing a transparent shell having a shape replicating a human heart, the transparent shell containing a first plurality of nodes connected along a first electrical pathway corresponding to an actual electrical network of a living heart, a second plurality of nodes connected along a second electrical pathway corresponding to a conceptual electrical phenomenon of a living heart, a first plurality of light emitters disposed along the first electrical pathway, the first plurality of light emitters demonstrating at least one of the physiological cardiac events, the cardiac pathologies, and the cardiac electrophysiologic patterns; and
    demonstrating, using at least the first plurality of light emitters, at least one of the physiological cardiac events, cardiac axes, cardiac pathologies, cardiac electrophysiological patterns related to physiological cardiac events, and cardiac electrophysiological patterns related to cardiac pathologies, based on the user input.

11. The method of claim 10, further comprising illustrating, using a display device, an electrocardiogram corresponding to the at least one of the physiological cardiac events, cardiac axes, cardiac pathologies, cardiac electrophysiological patterns related to physiological cardiac events, and cardiac electrophysiological patterns related to cardiac pathologies.

12. The method of claim 10, wherein the transparent shell is divided into multiple areas corresponding to at least one of cardiac anatomical references, wherein the multiple areas comprise a third group of light emitters, the third group of light emitters demonstrating different cardiac pathologies based on the user input.

13. The method of claim 10, wherein at least two of the first plurality of nodes are each in electrical communication with a button operable by the user for completing the electrical pathways, and wherein each complete electrical pathway corresponds to at least one of the physiological cardiac events, the related pathologies, and the cardiac electrophysiologic patterns.

14. The method of claim 10, wherein the user input is provided using a control panel connected to the microcontroller.

15. The method of claim 10, wherein the user input comprises an action corresponding to the different activities of the heart, and wherein the action is selected from a group consisting of stopping, slowing down electrical signal conductions, speeding up electrical signal conductions, creating a bypass, creating electrical signal reentry, initiating a normal ectopic event, initiating an altered ectopic event, and demonstrating a cardiac axis vector.

16. The method of claim 10, wherein the conceptual electrical phenomenon of a living heart is a cardiac axis.

17. The method of claim 16, wherein the transparent shell further comprising a second plurality of light emitters disposed along the second electrical pathway, the second plurality of light emitters demonstrating a cardiac axis vector.

* * * * *